United States Patent
Chalvignac

(10) Patent No.: US 6,722,359 B2
(45) Date of Patent: Apr. 20, 2004

(54) APPARATUS FOR ASSISTANCE FOR VENTING A PATIENT

(75) Inventor: Philippe Chalvignac, Achères-la-Forêt (FR)

(73) Assignee: Societe d'Applications Industrielles Medicales et Electronique (Saime), Savigny le Temple (FR)

( * ) Notice: Subject to any disclaimer, the term of this patent is extended or adjusted under 35 U.S.C. 154(b) by 201 days.

(21) Appl. No.: 09/917,898

(22) Filed: Jul. 31, 2001

(65) Prior Publication Data

US 2002/0014239 A1 Feb. 7, 2002

(30) Foreign Application Priority Data

Jul. 31, 2000 (FR) .............................. 00 10036

(51) Int. Cl.$^7$ .......................... A61M 16/00; A62B 7/00
(52) U.S. Cl. ........................................ 128/18; 128/22
(58) Field of Search ................... 128/204.21, 145.8, 128/200, 202.28, 204.13

(56) References Cited

U.S. PATENT DOCUMENTS 3,972,327 A * 8/1976 Ernst et al. ............... 128/145.8
5,370,112 A * 12/1994 Perkins ..................... 128/204.21

FOREIGN PATENT DOCUMENTS

WO      WO 96/11717      4/1996

* cited by examiner

Primary Examiner—Henry Bennett
Assistant Examiner—Sabrina Dagostino
(74) Attorney, Agent, or Firm—Young & Thompson

(57) ABSTRACT

An apparatus for assisting with ventilating a patient breathing in successive cycles, each of the cycles includes a phase of inhalation and a phase of exhalation. The apparatus includes a pressurized gas source, an outlet orifice of the gas source supplies a stream of pressurized gas. The apparatus also includes a gas stream distribution unit that has a transmission circuit which connects the gas source to a main inhalation pipe. The apparatus further includes an inhalation valve for regulating the gas stream and which is interposed in the transmission circuit and is controlled by a control circuit of the apparatus particularly as a function of the values of the flow rate inhalation valve is produced in the form of a rotary directional-control valve.

26 Claims, 11 Drawing Sheets

APPARATUS FOR ASSISTANCE FOR VENTING A PATIENT

BACKGROUND OF THE INVENTION

The invention relates to an apparatus for assistance for venting a patient.

The invention relates more specifically to an apparatus for assisting with ventilating a patient breathing in successive cycles, each of which comprises a phase of inhalation and a phase of exhalation.

Numerous types of apparatus exist for assisting with ventilation, these also being known as respirators, which make it possible to alleviate respiratory problems by, in particular, giving the patient insufflatory assistance during the inhalation phases.

The patient generally wears on his face a mask which covers his nose and mouth and to which the inhalation circuit is connected so as, in particular, to force the patient's inhalation.

In order that for it to be useable for various types of disorder, the apparatus for assisting with ventilation has to be able to operate according to different types of ventilation assistance mode, particularly a mode of the volumetric ventilation type, a mode of the percussive ventilation type and a mode of the barometric ventilation type.

In the volumetric-type ventilation assistance mode, the assistance apparatus needs to transmit a constant and/or determined volume of air to the patient. The air flow rate supplied to the patient during the inhalation phase may be constant, decreasing, increasing, sinusoidal, etc.

The value of the flow rate to be transmitted to the patient can vary across a wide range of values which may stretch from 5 to 150 liters per minute. In all cases, it has to be perfectly controlled. In addition, the duration of the increase in flow rate when switching from the patient's exhalation phase to his inhalation phase, and the time taken for the flow rate to reduce when switching from the patient's inhalation phase to his exhalation phase needs to be as short as possible.

In the barometric-type ventilation assistance mode, the assistance apparatus needs to transmit gas, particularly a volume of gas, to the patient at a pressure which is constant throughout the patient's inhalation phase. In this type of ventilation, the pressurized gas flow rate is higher than it is in the volumetric ventilation type of mode. The time taken for the gas pressure to rise needs to be as short as possible. However, ventilation assistance apparatus, particularly ventilation apparatus for use in the home, find it difficult to reduce this time to a minimum.

In the third, percussive ventilation assistance mode, the ventilation assistance apparatus needs to transmit to the patient a gas flow rate which is amplitude-modulated during the various phases of the ventilation. The frequency of the oscillations, which may be between 1 and 10 bursts per second, is difficult to obtain with assistance apparatus of the known type. This is because the inertia of the inhalation valves does not always allow the aforementioned requirements to be met.

In addition, the apparatus for assisting with ventilation requires an electric power supply to allow elements such as the pressurized gas source which may be a bellows or a fanwheel to operate.

Ventilation apparatus, particularly ventilation apparatus for use in the home, does not always allow the use of the aforementioned three modes.

Such apparatus may be used in a hospital environment or at the patients' home. In either case, it may be used by ambulatory patients, so as not to impede their mobility, and it is then advantageous for them to be offered autonomous apparatus for assisting with ventilation.

In this case, it is necessary to fit the apparatus with batteries that accumulate electric energy. However, the autonomy is greatly limited because of the bulk, weight and cost of such batteries which have to be incorporated into the ventilation assistance apparatus.

In addition, the very diverse range of disorders treated by apparatus for assisting with ventilation means that each apparatus has to be somewhat specialized. Thus, there is a category of disorders that corresponds to each type of apparatus. This reduces the number of pieces of apparatus produced for each category and increases the design and manufacture costs.

SUMMARY OF THE INVENTION

With a view to overcoming these drawbacks, the invention proposes an apparatus for assisting with ventilating a patient breathing in successive cycles, each of which comprises a phase of inhalation and a phase of exhalation, of the type comprising:

a pressurized gas source, an outlet orifice of which supplies a stream of pressurized gas intended to be transmitted to the upper airways of the patient;

a pressurized gas stream distribution unit which comprises a transmission circuit which connects the outlet orifice of the gas source to a first free end of a main inhalation pipe, to the second free end of which is fixed a mask, particularly of the face mask type, intended to be worn by the patient; and an inhalation valve for regulating the said gas stream and which is interposed in the transmission circuit, and is controlled by a control circuit of the apparatus particularly as a function of the values of the flow rate and of the pressure of the gas in the main pipe, characterized in that the inhalation valve is produced in the form of a rotary directional-control valve.

According to other features of the invention:

the inhalation valve for regulating the gas stream comprises a tubular valve body comprising, in its wall, a longitudinal oblong opening which allows the stream of gas from the outlet orifice of the gas source to be transmitted to the first free end of the main inhalation pipe and comprises a spool which is mounted so that it can turn in the body, which is closed at one of its axial ends, and of which an axial end edge, at the opposite end to its closed end, is profiled so that as the spool is turned, the passage cross section of the oblong opening allowing the transmission of the gas stream is varied progressively;

the outlet orifice of the gas source opens into the first free end of a first hole, the second free end of which is plugged by the closed end of the spool and the distribution unit has a recess which opens, on the one hand, opposite the longitudinal oblong opening which it complements, and on the other hand, into a second blind hole to the free end of which the first free end of the main inhalation pipe is fixed;

the spool is turned by a motor, particularly of the stepping type, controlled by the control circuit of the apparatus;

the spool has a device for indexing its angular position;

when the apparatus operates in the volumetric ventilation respiratory assistance mode, during the inhalation phase of which the apparatus has to provide the patient with a predetermined volume of gas, the control circuit of the apparatus controls the angular position of the spool and the pressure supplied by the gas source so that the passage cross section allows the predetermined volume of gas to be transmitted to the patient;

when the apparatus operates in barometric ventilation respiratory assistance mode, during the inhalation phase of which the apparatus has to supply the patient with a gas at a predetermined pressure, the control circuit of the apparatus controls the angular position of the spool so that the passage cross section corresponds to the entirety of the oblong opening and the control circuit of the apparatus controls the pressure supplied by the gas source so that the pressure of the gas in the inhalation pipe is the predetermined gas pressure;

when the apparatus operates in percussive ventilation assistance mode, during the inhalation phase of which the apparatus has to provide the patient with a flow rate which oscillates about a predetermined gas flow rate, the control circuit of the apparatus controls the switching of the angular position of the spool back and forth about a predetermined position that corresponds to the predetermined flow rate and controls the pressure supplied by the gas source;

the pressurized gas source comprises a rotary electric machine controlled in terms of speed by the control circuit, a free end of the rotor of which drives the rotation of a bladed wheel which drives the gas stream through a guide volute of a casing when the rotary electric machine is electrically powered;

the casing has at least one injection point, opening into the volute, for ejecting at least one compressed gas which is supplied by another upstream pressure source, at a second pressure higher than the first pressure, and the compressed gas at the second pressure is capable of driving the rotation of bladed wheel and of the rotor of the rotary electric machine so that the pressurized gas is supplied to the patient at the first pressure and the rotary electric machine acts as an electricity generator and produces electrical energy;

the stream of at least one gas at a second pressure is injected into the casing in a direction more or less tangential to the volute;

the upstream pressure source at least partially consists of a pressurized gas circuit available in a hospital environment;

the source of pressure comprises a pressurized gas reservoir;

the reservoir is incorporated into the apparatus for assisting with ventilation;

the gas at the second pressure is made up at least partially of air;

the compressed gas at the second pressure is made up at least partially of a therapeutic gas;

the therapeutic gas is oxygen;

means for regulating the pressure are inserted between the said other upstream pressure source and injection point;

the apparatus comprises a valve for metering the compressed gas at the second pressure, the opening of which valve is controlled in proportion with the opening of the inhalation valve;

the electrical energy supplied by the rotary electric machine, operating as a generator, at least partially powers the electricity-consuming systems of the apparatus;

the electrical energy produced by the rotary electric machine, operating as a generator, powers and at least partially charges an accumulator battery of the apparatus;

the electrical energy produced by the rotary electric machine is more than the electrical energy consumed by the electricity-consuming systems, so that the apparatus for assisting with respiratory ventilation is autonomous;

the distribution unit comprises controlling means which can order the opening and closing of an exhalation valve which is arranged with equal preference in the inhalation pipe of a single circuit or in the exhalation pipe of a double circuit;

when the apparatus has a double circuit, the exhalation valve is arranged in a module which is fixed to the distribution unit and comprises a pipe for connecting the controlling means to the exhalation valve;

the controlling means allow a positive exhalation pressure to be applied to the exhalation valve, and the positive exhalation pressure is provided by a fan;

the distribution unit comprises measuring means which determine the flow rate of gas flowing, during the exhalation phase, through the inhalation pipe of a single circuit or through the exhalation pipe of a double circuit;

when the apparatus has a double circuit it comprises a module which is fixed to the distribution unit and comprises at least one pipe connecting the measuring means to the exhalation pipe.

BRIEF DESCRIPTION OF THE DRAWINGS

Other features and advantages of the invention will become apparent from reading the detailed description which follows, for an understanding of which reference will be made to the appended drawings among which.

In the remainder of the description, elements which are identical or similar will be denoted by the same reference figures.

DETAILED DESCRIPTION OF THE PREFERRED

Figure 1:
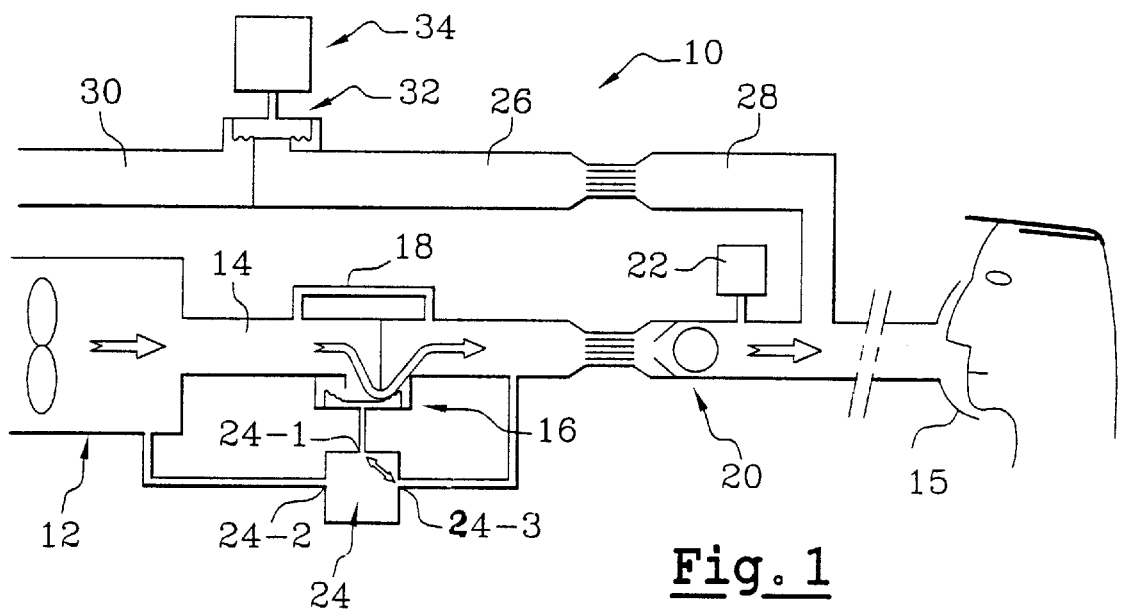
FIG. 1 is a schematic and simplified view of an apparatus for assisting with ventilation produced according to the state of the art, the apparatus being illustrated during an inhalation phase.

FIG. 1 illustrates an apparatus for assisting with the ventilation of a patient produced according to the state of the art.

The apparatus 10 first of all comprises a pressurized air source 12 which is, for example, produced in the form of a motorized fan unit or fanwheel, with an electric motor, which constantly supplies pressurized air to a main inhalation pipe 14 a downstream end of which is connected, for example, to a mask 15 which covers the upper airways of the patent, that is to say his nose and mouth.

Inserted in the inhalation pipe 14 is an inhalation valve 16 which here is produced in the form of a pneumatically operated balloon valve. The inhalation valve 16 is open during the patient's inhalation phases and closed during the exhalation phases. However, a bypass pipe 18 bypasses the inhalation valve 16 so as to allow a small leakage flow rate to pass through the inhalation pipe 14 even during the exhalation phases so as, for example, to compensate for air leaks at the patient's mask 15.

Downstream of the inhalation valve 16 there are, in succession, in the inhalation pipe 14, a nonreturn valve 20 which prevents gas exhaled by the patient from being able to return towards the pressurized air source, and a pressure and flow rate sensor 22.

To operate the inhalation valve 16, it can be seen that there is an electrically operated valve 24 which has three inlets 24-1, 24-2 and 24-3, each of which is connected by a line to, respectively, the balloon of the inhalation valve 16, the outlet of the pressurized air source 12, and the inhalation pipe 14 downstream of the inhalation valve 16.

The electrically operated valve 24 that operates the inhalation valve 16 can therefore be switched either so that its inlet 24-1 communicates with its inlet 24-2 or so that its inlet 24-1 communicates with its inlet 24-3. In the former case, the pressure in the balloon of the inhalation valve 16 is then the pressure supplied by the pressure source 12, which causes the inhalation valve 16 to close. On the other hand, when the electrically operated valve 24 places its inlets 24-1 and 24-3 in communication, according to FIG. 1, the inhalation valve 16 opens and allows the pressurized air or mixture supplied by the pressure source 12 to be conveyed to the patient.

For further details regarding the operation of the inhalation circuit, reference can be usefully made to document FR-A-2 760 196 which describes an inhalation valve 16 of the same type.

The apparatus 10 for assisting with respiration also comprises an exhalation pipe 26, an upstream end 28 of which is connected, for example, to the patient's mask 15 and a downstream end 30 of which opens, for example, into the atmosphere.

In a known way, an exhalation valve 32, produced in the form of a balloon valve, is inserted in the exhalation pipe 26.

The exhalation valve 32 is closed during the patient's inhalation phases and is open, partially or completely, during the exhalation phases. The pressure in the balloon of the exhalation valve 32, which determines the opening or closing of the valve 32, is controlled by a control circuit 34.

The way in which the control circuit 34 that controls the exhalation valve 32 works will now be described in greater detail.

During an inhalation phase, the balloon of the exhalation valve 32 is inflated. Thus, the exhalation valve 32 is closed, preventing any gas from flowing through the exhalation pipe 26.

At the start of the exhalation phase, the balloon of the exhalation valve 32 is deflated so as to allow gas to flow through the exhalation pipe 26.

When there is a desire to impose a positive exhalation pressure on the patient, it is then necessary, quite soon after the start of the exhalation phase and, for example, after a period of between 100 and 200 milliseconds, to cause the deflation of the balloon of the exhalation valve 32 to stop.

It is possible, for example, to choose to stop the deflating of the balloon of the exhalation valve 32 when the pressure in the balloon of the valve 32 has dropped to a value just 3 millibar higher than the value chosen for the positive exhalation pressure.

Thus, the exhalation valve 32 opens only when the effort exerted by the air exhaled by the patient upstream of the exhalation valve 32 in the exhalation pipe 26 becomes higher than a threshold value that can be set by adjusting the pressure in the balloon of the exhalation valve 32.

However, such a type of apparatus 10 for assisting with ventilation does not allow optimum operation as described before.

In order to remedy these drawbacks, the invention proposes for the apparatus 10 for assisting with the ventilating of the patient to comprise a pressurized gas flow distribution unit 50 which comprises a transmission circuit 52 connecting the outlet orifice of the pressurized gas source 12 to a first free end 57 of the main inhalation pipe 14, to the second end of which the mask 15 intended to be worn by the patient is fixed.

Figure 2:
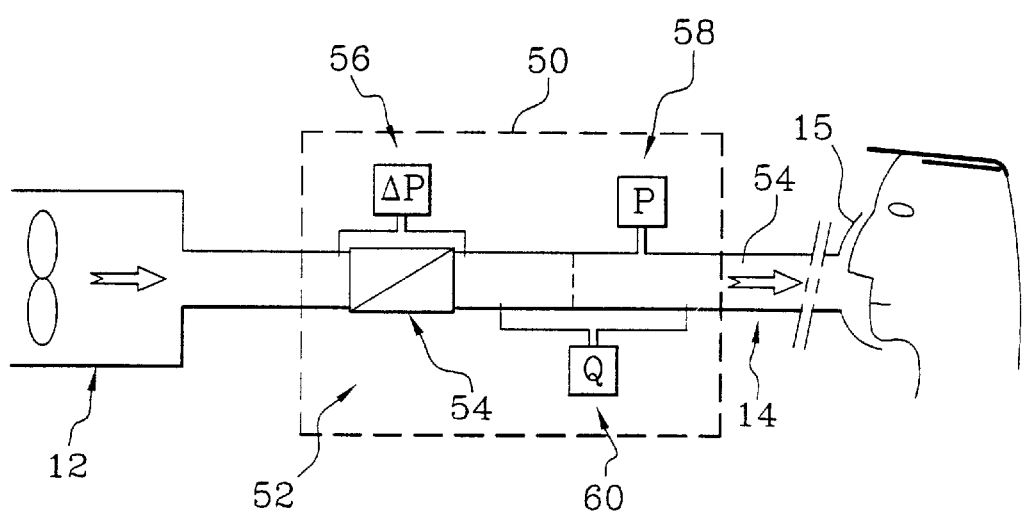
FIG. 2 is a schematic and simplified view of part of an apparatus for assisting with ventilation produced according to the teachings of the invention.
Figure 3:
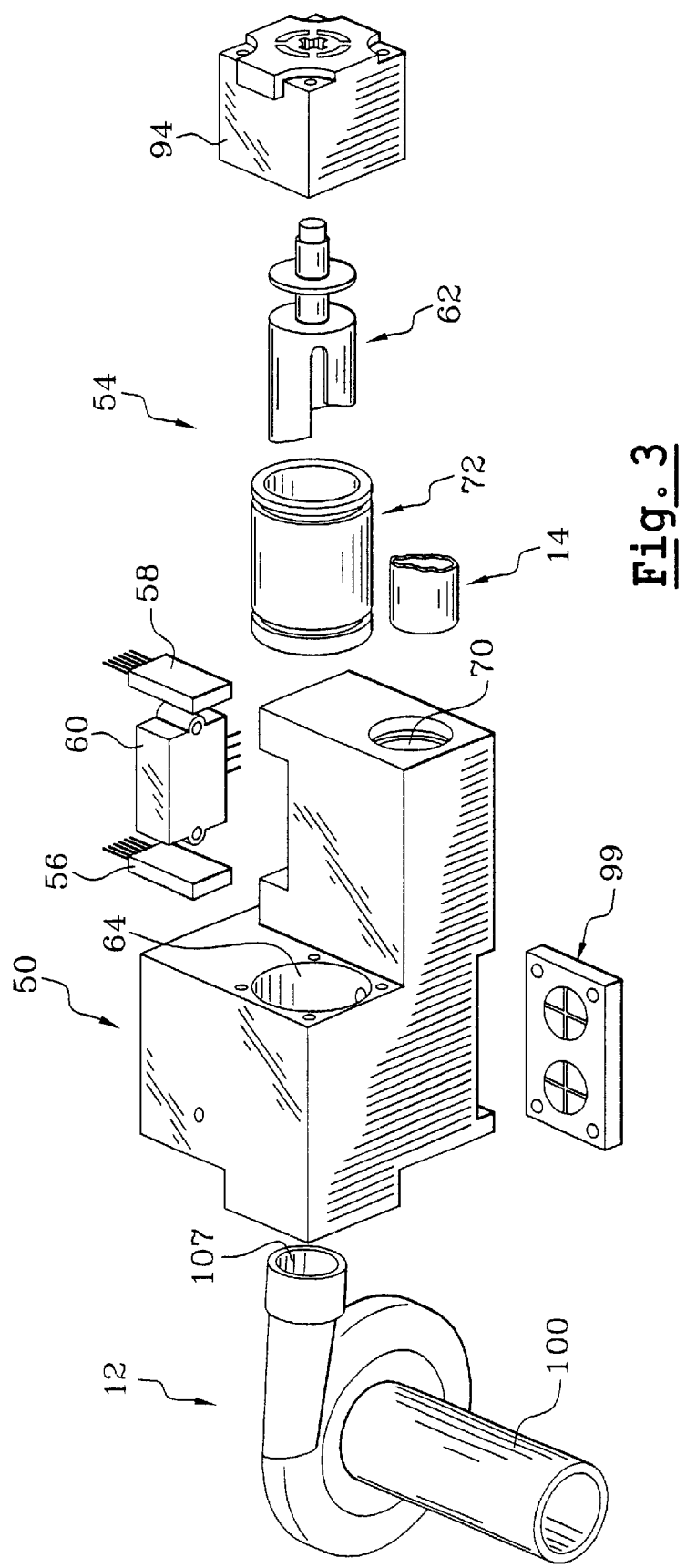
FIG. 3 is an exploded perspective view which mainly depicts the pressurized gas flow distribution unit produced according to the invention, and the pressurized gas source.
Figure 4:
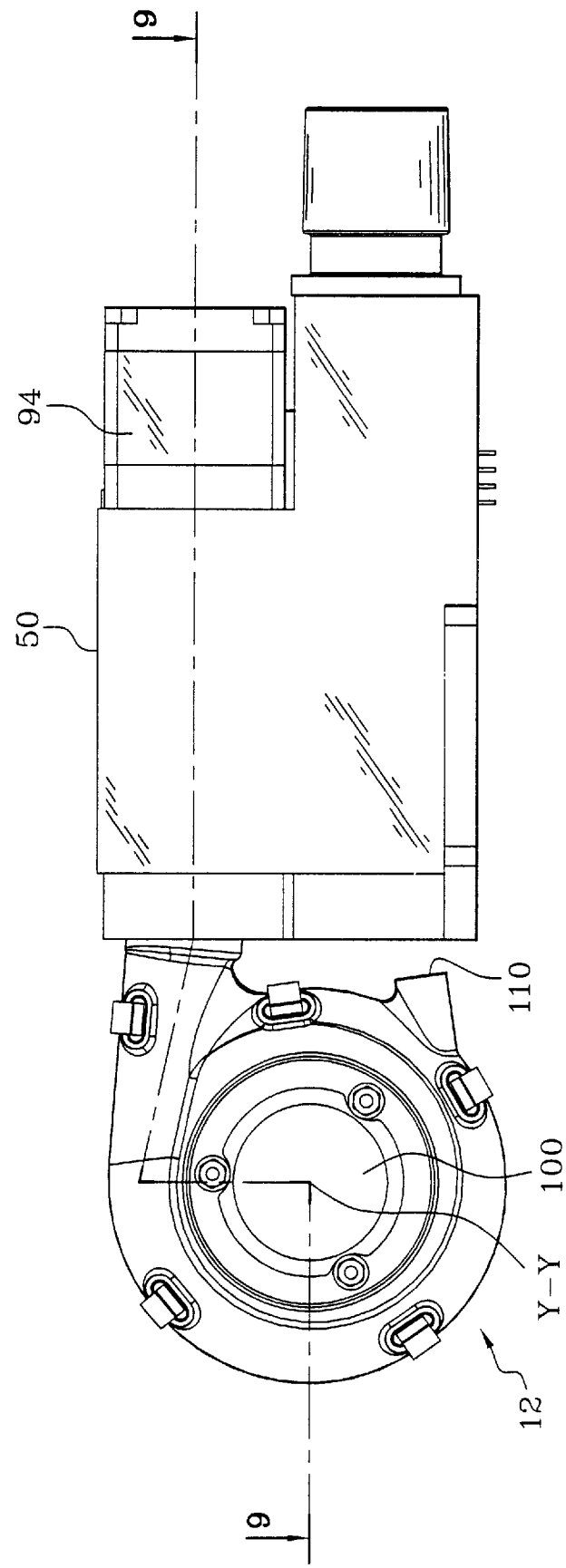
FIGS. 4 to 8 depict the various external views of the pressurized gas source assembled with the pressurized gas flow distribution unit, this assembly being illustrated respectively in a view from the front, in a view from above, in a view from underneath and in side views.

Apparatus 10 such as this for assisting with ventilation is depicted in FIG. 2.

In order to regulate and modulate precisely the stream of gas between the pressurized gas source 12 and the inhalation pipe 14, an inhalation valve 54 is inserted in the transmission circuit 52.

The inhalation valve 54 is controlled by a control circuit, not depicted, of the apparatus, particularly according to values of the flow rate and pressure of the gas in the transmission circuit 52. The control circuit comprises electronic circuits which, in particular, make it possible to process and formulate electrical signals.

For this purpose, first measurement means 56 make it possible to determine the pressure drop caused by the inhalation valve 54. The first measurement means 56 transmit to the control circuit information representing the pressure difference between the upstream and downstream sides of the inhalation valve 54.

The measurement means 56 may consist of a differential pressure sensor fixed to the distribution unit 50 and which is connected to the transmission circuit 52 by a first duct and a second duct or passage, none of these depicted, upstream and downstream of the inhalation valve 54, respectively.

Second measurement means 58 make it possible to determine the pressure near the downstream end of the transmission circuit 52. The second measurement means 58 transmit to the control circuit information representing the pressure in the inhalation pipe 14.

The second measurement means 58 may consist of a pressure sensor which is connected to the transmission circuit 52.

They may also consist of a differential pressure sensor similar to the one used for the first pressure means 56. The use of such a sensor makes it possible to reduce the number of components in the ventilation assistance apparatus 10, and therefore to reduce its cost of manufacture. In this case, the differential pressure sensor comprises two pressure inlets, one being connected, by a duct not depicted, to the transmission circuit 52, the other sensor being connected directly to the atmosphere.

Third measurement means 60 make it possible to determine the flow rate of the gas stream flowing through the transmission circuit 52 and which more or less corresponds to the gas stream transmitted to the patient's mask 15.

According to FIG. 2, the measurement means 60 comprise two pressure sensors which are located one on each side of a member whose function is to cause a pressure drop.

According to the teachings of the invention and in order to regulate optimally the stream of gas flowing through the transmission circuit 52, the inhalation valve 54 is of the rotary spool type.

It makes it possible to vary the passage cross section for the stream of gas passing through it by turning a moving part driven by a rapid drive device having low inertia, so as, in particular, to reduce the time taken to open and to close the valve when switching from the inhalation phase to the exhalation phase, and vice versa.

The inhalation valve 54 is in the form of a rotary distributor which therefore has a tubular body 62 aligned axially with the outlet orifice of the gas source 12 of axis X—X.

Figure 9:
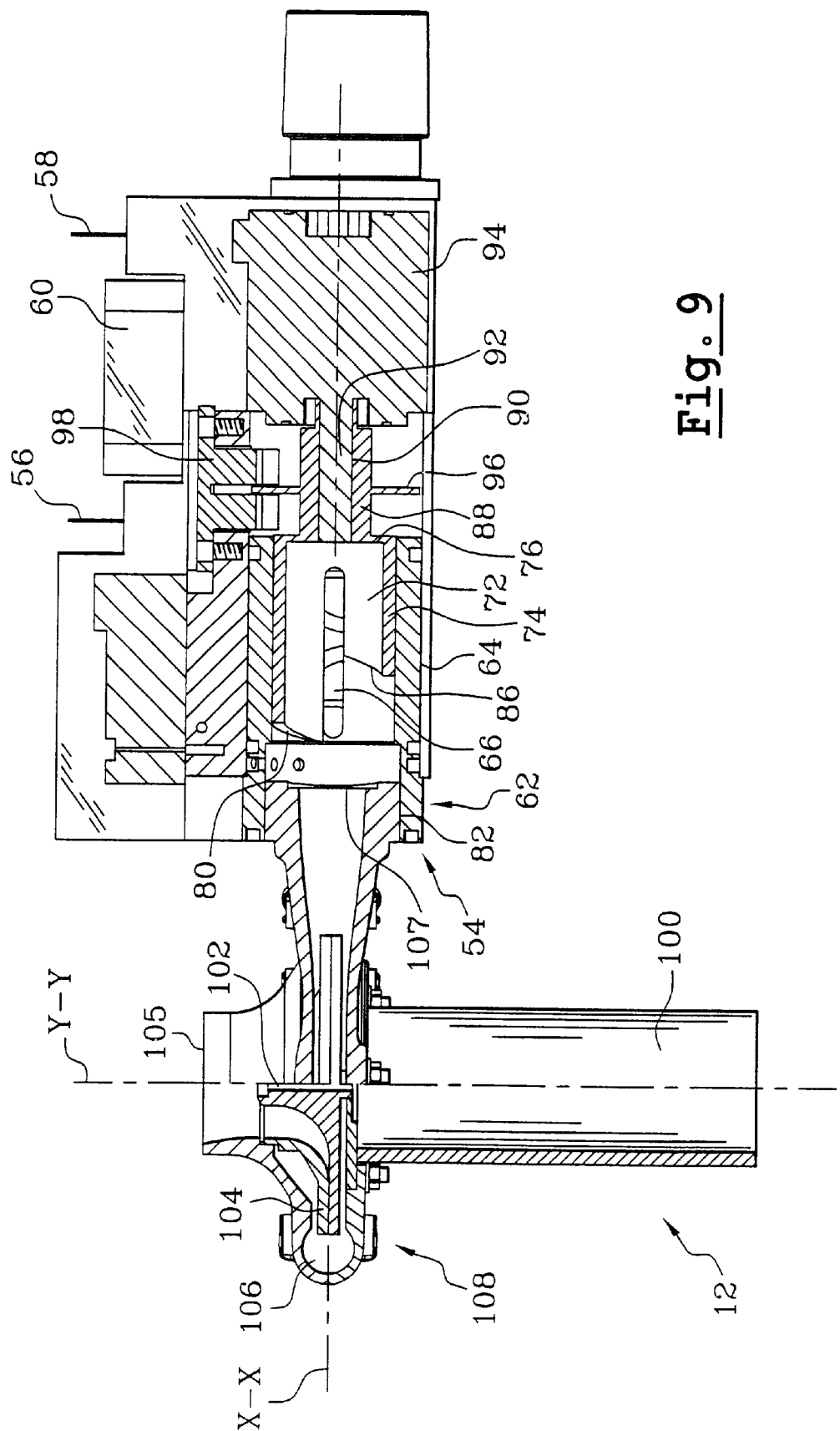
FIG. 9 is a view in section of the pressurized gas source and of the gas flow distribution unit on the line 9-9 of FIG. 4.
Figure 10:
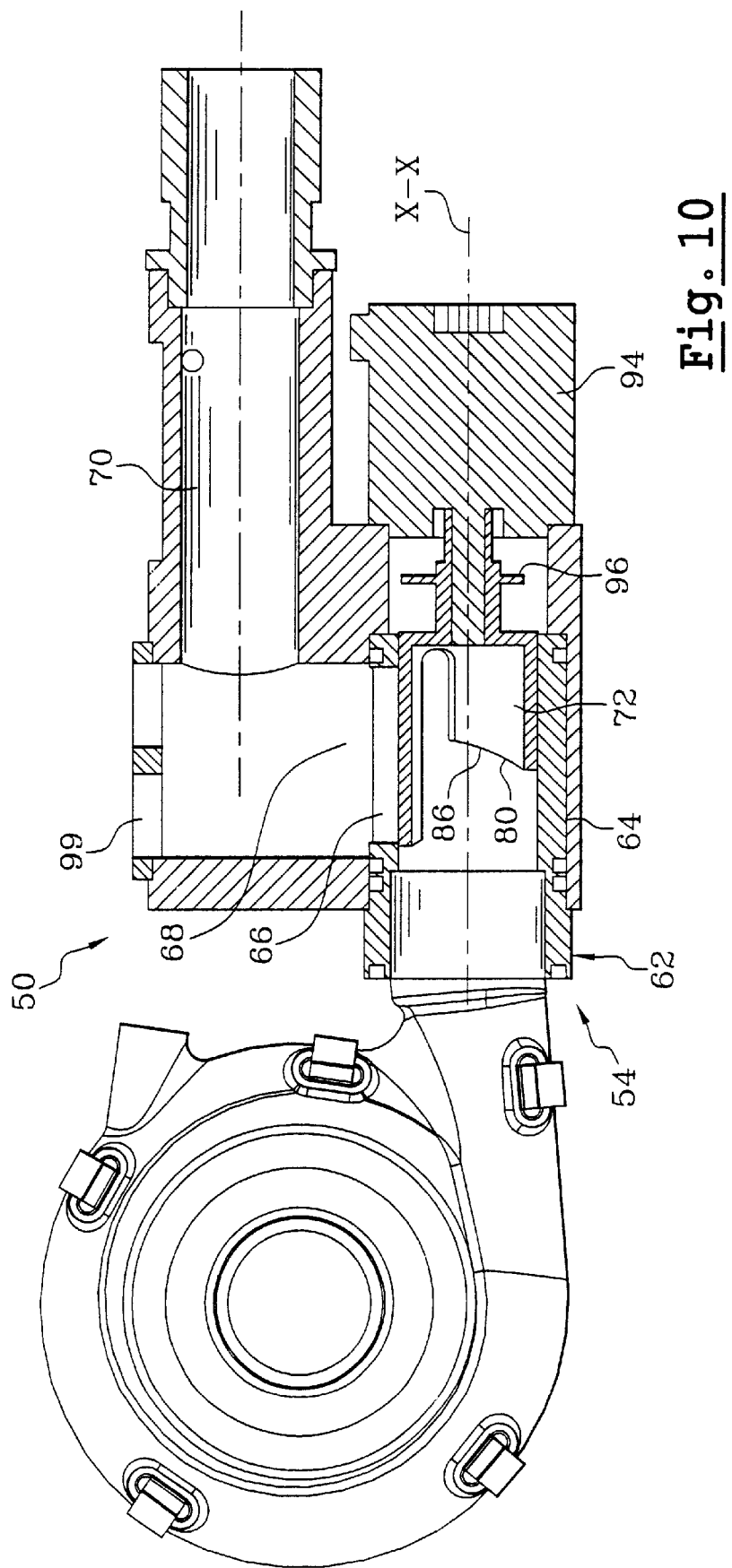
FIG. 10 is a view in part section of the pressurized gas source and of the gas flow distribution unit on the line 10-10 of FIG. 6.

According to FIGS. 9 and 10, the tubular body 62 is housed in a sealed manner in a first hole 64 in the distribution unit 50.

The tubular body 62 comprises, in its annular cylindrical wall, a first oblong opening, or slot 66, oriented axially. A recess 68 is made in the distribution unit 50, facing the oblong opening 66.

The oblong opening 66 and the recess 68 thus make it possible for the inside of the tubular body 62 to be connected to a second hole 70 produced axially in the distribution unit 50.

According to FIG. 10, the two holes 64 and 70 are parallel and superposed with one another.

The oblong opening 66 defines the maximum passage cross section for the stream of gas through the inhalation valve 54. The maximum passage cross section thus defined is greater than the passage cross section needed to transmit the maximum volume of gas when the apparatus 10 for assisting with ventilation operates in volumetric ventilation respiratory assistance mode.

In order to manage the flow rate of pressurized gas passing through the valve 54, that is to say the flow rate of gas transmitted to the airways of the patient, a spool 72 is mounted so that it can turn about the axis X—X.

The rotary spool 72 has a skirt or sleeve 74 which extends axially from a rear transverse wall 76 for closing off the downstream end 78 of the tubular body 62. Thus, the pressurized air stream introduced into the first hole 64 can escape only through the oblong opening 66 and the recess 68.

The skirt 74 thus extends axially from the rear transverse wall 76 towards the upstream end of the former, from the hole 64. Its maximum axial dimension is defined so that a front part of the skirt 74 can, in the closed position, completely shut off the oblong opening 66 of the tubular body 62.

To simplify the sealing of the first hole 64, the outlet orifice of the gas source 12 is mounted in a sealed manner directly inside an orifice 82 in the upstream free end of the tubular body 62.

The front axial end edge 80 of the skirt 74, which is the opposite end to the transverse wall 76, is profiled.

In general, the profile of the axial end edge 80 has two zones.

A first zone consists of an axial groove 84 which extends to near the rear transverse wall 76 of the spool 72 so that when the spool 72 is in an angular position known as the wide-open position, the axial groove 84 extends facing the oblong opening 66 so that the passage cross section for the stream corresponds to the maximum passage cross section defined earlier. Thus, the width of the axial groove 84 may correspond to a sector subtended by an angle of about twenty degrees.

The second zone corresponds to a curve in the overall form of a spiral 86 which extends between the two parallel axial edges of the groove 84.

Figure 11:
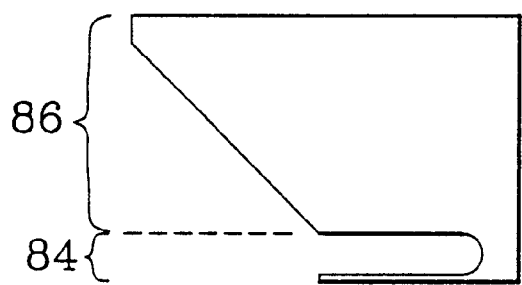
FIG. 11 is a developed schematic view of the rotary spool of the inhalation valve of the distribution unit.

FIG. 11 depicts an example of the development of the skirt 74, more clearly showing the two zones and, in particular, the profile of the spiral 86.

Thus, turning the spool causes the oblong opening 66 to be shut off in such a way as to vary the passage cross section for the gas stream.

The spool 72 has a shank 88 which extends axially from the transverse wall 76 in a rear direction away from the pressurized gas source 12. A hole 90 of axis X—X is made in the shank 88 so as to allow the passage of a member 92 for turning the spool 72. The member 92 is prevented from turning with respect to the shank 88. Advantageously, the member 92 is mounted snugly in the other axial hole 90.

The member 92, which turns the spool 72, here is the output shaft of an electric motor 94 of the stepping type. The rotating of the motor 94 is controlled by the control circuit of the apparatus 10.

In order to angularly index the position of the spool 72, and therefore that of the spiral 86, with respect to the first oblong opening 66, a transverse flange 96 is arranged on the shank 88. On the periphery of its radial faces, the flange 96 has devices enabling its angular position to be identified.

The flange 96 may therefore correspond to an encoder wheel which collaborates with an optical device 98, partially depicted in FIG. 9.

Thus, in a known general way, the optical device 98 transmits to the control circuit information representing the angular position of the spool 72.

Use of such an inhalation valve 54 exhibits numerous advantages.

The way in which the apparatus 10 for assisting with ventilation works and the way in which the stream of gas transmitted to the upper airways of the patient by the inhalation valve 54 is regulated are as follows.

Figure 12:
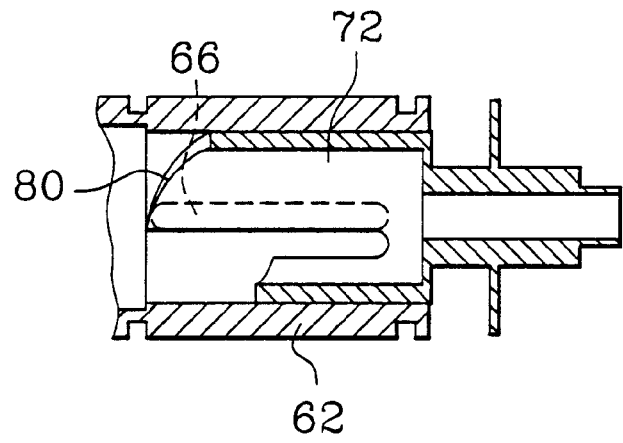
FIG. 12 is a detailed part view of the view depicted in FIG. 9, the inhalation valve being in a closed position.

In the exhalation phase, the spool 72 of the inhalation valve 54 is in a position said to be closed, depicted in FIG. 12. In this case, the skirt 74 completely blocks off the oblong opening 66.

Advantageously, in this position, the front end edge 80 of the skirt 74 does not completely shut off the first oblong opening 66, so as to allow a gas flow rate known as the leakage flow rate to flow constantly through the passage cross section.

The leakage flow rate which flows through the inhalation pipe 14 in particular makes it possible to compensate for leakages at the patient's mask 15.

Figure 13:
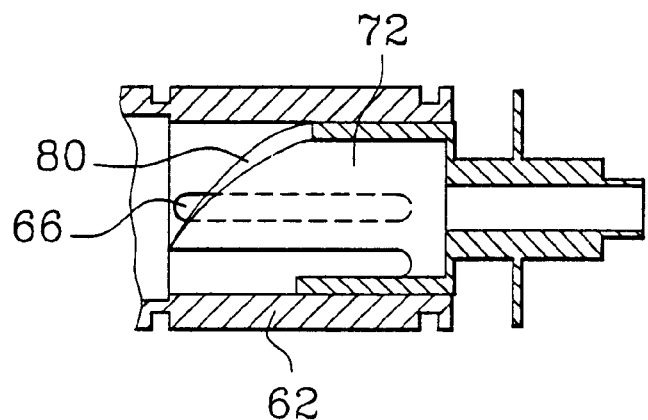
FIG. 13 is a view similar to the one depicted in the previous figure, the inhalation valve being in a partially open position.

When the apparatus 10 for assisting with ventilation switches to the inhalation phase, the motor 94 turns the spool 72 to a predetermined position depicted in FIG. 13 so as to increase the passage cross section for the gas in the oblong opening 66.

When the pressure difference between the upstream and downstream sides of the inhalation valve 54 is constant, the gas flow rate passing through the inhalation valve 54 is constant and is proportional to the passage cross section for the stream of gas through the oblong opening 66. Thus, the gas flow rate transmitted to the upper airways of the patient is determined accurately.

The switch from the closed position to the predetermined position needs to be as quick as possible. This is because it is at the start of the inhalation phase that the gas flow rate inhaled by the patient is the greatest. When the switch from the closed position to the predetermined position is not quick enough, the patient has to make an effort to inhale, which is a problem.

The speed of movement depends on several parameters, particularly on the inertia of the moving parts, on characteristics of the motor 94, and on the angle through which the spool is to be turned.

In order to optimize the performance of the apparatus 10 for assisting with ventilation, the moving parts are made of materials and with shapes which allow their mass and their inertia to be reduced as far as possible.

The motor 94 allows high acceleration so as to reach its maximum speed as soon as possible.

The angle through which the spool 72 is to be turned depends on the profile of its front end edge 80 and on the type of ventilation required by the patient.

When the apparatus 10 for assisting with ventilation operates in volumetric ventilation respiratory assistance mode, it has to supply the patient with a predetermined volume of gas.

During the inhalation phase, the gas flow rate transmitted to the patient may be constant, certain disorders requiring the flow rate to change, for example to increase, to decrease, or to follow a sinusoidal form.

For this type of ventilation, the control circuit of the apparatus 10 controls the pressure of the gas at the outlet of the gas source so that the pressure difference between the upstream and downstream sides of the inhalation valve 54 is kept constant. In addition, the control circuit of the apparatus 10 controls the turning of the spool 72 so that the passage cross section of the oblong orifice 66 allows the predetermined volume of gas to be transmitted.

When the flow rate needs to be constant during the inhalation phase, the motor 94 positions the spool 72 in the predetermined position that allows the predetermined volume of gas to be transmitted. The angle through which the spool 72 is rotated, which angle depends on the profile of the front end edge 80, is always less than one turn.

If the gas flow rate needs to vary during the inhalation phase, the motor 94 positions the spool 72 in an initial position, then turns it during the inhalation phase so that the volume of gas transmitted during the inhalation phase corresponds to the predetermined volume of gas.

When the apparatus 10 for assisting with ventilation operates in barometric ventilation respiratory assistance mode, it has to supply the patient with gas at a predetermined pressure.

In this case, the gas flow rate transmitted to the patient may be high. In addition, it is at the start of the inhalation phase that the demand for gas, and therefore the gas flow rate, by the patient is the highest.

It is therefore necessary for the inhalation valve 54 to allow the maximum gas flow rate to pass quickly through the oblong opening 66.

To achieve this, the motor 94 turns the spool 72 by a few degrees so that the groove 84 faces the oblong opening 66. Thus, a small rotation of the motor 94 makes it possible to switch from the position in which the inhalation valve 54 is closed to the wide-open position allowing the maximum flow rate to be transmitted.

During ventilation of this type, the gas source 12 is controlled by the control circuit, on the basis of the value of the pressure in the inhalation pipe 14, which value is provided by the second measurement means 58.

According to an alternative, the oblong opening 66 is widened at one of its axial ends so as to increase the gas flow rate through the passage cross section.

In this case, it is necessary to increase slightly the angle through which the spool is turned so as to completely uncover the widened oblong opening 66.

Advantageously, the widening is produced on the section of the oblong opening 66 which is not uncovered by the skirt 74 when the inhalation valve 54 is in the wide-open position. Thus, the maximum flow rate that passes through it is increased in barometric mode whereas, in volumetric mode, the accuracy of regulation is not diminished.

When the apparatus 10 for assisting with ventilation operates in percussive ventilation respiratory assistance mode, during the inhalation phase of which the apparatus has to supply the patient with a flow rate which oscillates about a predetermined gas flow rate, the control circuit of the apparatus 10 controls switching of the position of the spool 72 back and forth about a predetermined angular position corresponding to the predetermined flow rate. The control circuit also allows control of the pressure supplied by the gas source 12 so as to ensure a constant pressure difference between the upstream and downstream sides of the inhalation valve 54.

Thus, the apparatus 10 for assisting ventilation according to the invention makes it possible accurately and quickly to regulate the stream of pressurized gas transmitted to the patient.

For safety reasons, the apparatus 10 for assisting with ventilation also comprises two vent valves 99. Thus, if the source 12 of pressurized gas or the inhalation valve 54 were to fail and shut off the circulation of the stream of air in the distribution unit 50 when the patient is in the inhalation phase, the vent valves 99 can open when the value of the depression in the second hole 70 is below a predetermined value. The patient can thus breathe in air from outside. In this case, an exhalation valve of the apparatus 10 is in the open position, so that the patient can exhale the air which he has breathed in through the valves 99.

The invention also proposes for the pressurized gas source 12 to comprise a rotary electric machine 100, of axis Y—Y, a free end of the rotor 102 of which is fixed to a bladed wheel 104.

The bladed wheel 104 is mounted to rotate about the axis Y—Y in a guide volute 106 of a casing 108.

When the rotary electric machine 100 is electrically powered, it causes the bladed wheel 104 to turn and this drives a stream of gas through the guide volute 106 from an axial air intake inlet 105 towards the outlet orifice 107. The gas stream is transmitted to the patient. The gas source 12 therefore operates in "fan" mode.

It is advantageous for the casing 108 to comprise at least one point 110, opening into the volute 106, for injecting at least one gas which is supplied by an upstream pressurized gas source, not depicted, at a second pressure higher than the first pressure of the gas transmitted to the patient, and which is here known as the boost gas.

The gas injected into the volute 106, at the injection point 110, at the second pressure, may then allow the bladed wheel 104 and the rotor 102 of the rotary electric machine 100 to be made to turn.

The rotary electric machine 100 therefore acts as a generator of electrical energy.

Advantageously, in order for the rotary electric machine to produce the maximum amount of electrical energy, the stream of at least one gas at a second pressure is injected into the casing 108 in a direction more or less tangential to the volute 106.

Such a gas source 12 therefore makes it possible to increase the autonomy of the ventilation assist apparatus 10. What happens is that the electrical energy produced can be used by all the components that consume electrical energy, such as the motor 94 and the control circuit. In addition, the electrical energy produced may even make it possible to power and recharge the accumulator batteries of the apparatus 10.

The upstream pressure source consists, for example, at least partially of a pressurized gas circuit available in a hospital environment.

The upstream pressure source may also supply the apparatus with a therapeutic gas such as oxygen.

The amount of therapeutic gas injected is advantageously metered by a metering valve comprising a body and a spool, in a similar way to the inhalation valve 54. Thus, this therapeutic-gas metering valve may be made to open in proportion with the extent to which the inhalation valve 54 is open.

When pressurized air is supplied continuously to the apparatus 10 for assisting with ventilation, the electrical energy produced by the rotary electric machine 100 may be enough to power the apparatus 10 for assisting with ventilation. In this case, main power to the apparatus 10 may be dispensed with. This makes the apparatus 10 easier to handle because it is not connected to the main power by a power leads.

The upstream pressure source may also be a reservoir of pressurized gas which may be situated close to the apparatus 10 for assisting with ventilation. The upstream pressure source may also be built into the apparatus 10.

Advantageously, pressure regulating means, not depicted, are inserted between the upstream pressure source and the injection point 110. Thus, the upstream pressure source can supply gas at a pressure higher than the pressure at which it is to be injected into the injection point 110, the pressure regulating means allowing the pressure of the gas injected to be adapted so as to achieve optimum output of the rotary electric machine 100.

The pressure regulating means may be a gas pressure reducer.

In order for the apparatus 10 for assisting with ventilation to be useable by a wide range of patients, that is to say both by patients who have a certain degree of mobility, such as able-bodied patients cared for at home, and by bedridden patients, particularly in a hospital environment, the invention proposes that the apparatus 10 for assisting with ventilation be of modular design.

Figure 14:
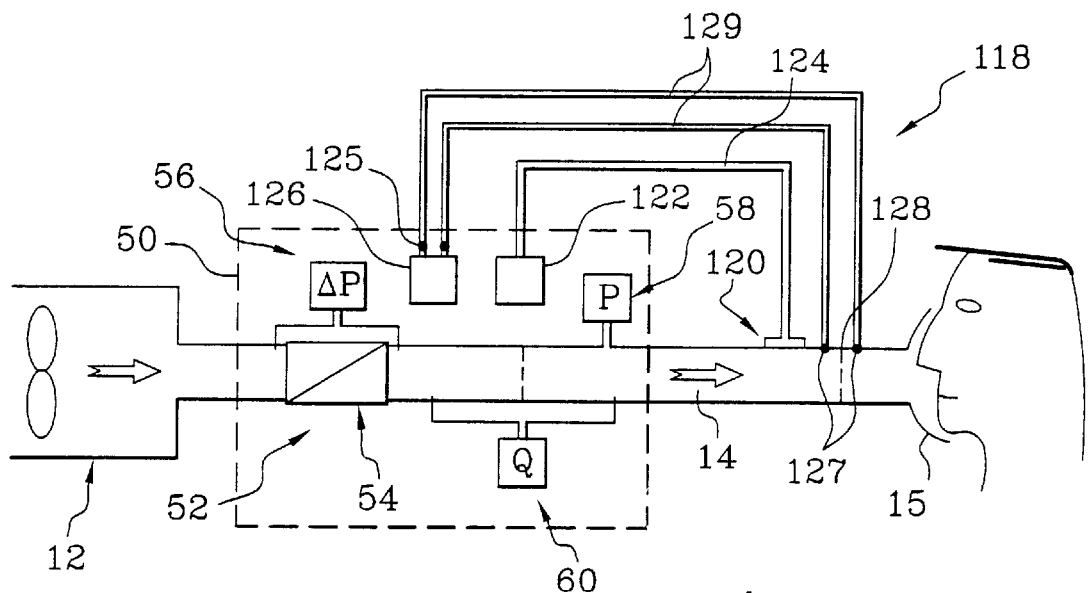
FIG. 14 is a view similar to the one depicted in FIG. 2, the apparatus for assisting with ventilation being equipped with a single circuit.

To this end, the apparatus 10 for assisting with ventilation is intended in particular for patients who have a certain degree of mobility and require simple, lightweight, easy-to-handle and robust equipment. The apparatus 10 for assisting with ventilation which then has a circuit known as a "single circuit" 118, that is to say that the inhalation pipe 14 near the patient has an exhalation valve 120 according to FIG. 14.

The exhalation valve 120 is ordered to remain closed during the inhalation phase and to open during the exhalation phase.

In certain cases, during the exhalation phase, it is necessary to apply a positive exhalation pressure to the exhalation valve 120 to compensate for a pressure intrinsic to the patient's lungs.

Thus, the distribution unit comprises controlling means 122 which, on the one hand, allow the exhalation valve 120 to be opened and closed during the patient's exhalation and inhalation phases and, on the other hand, control the value of the positive exhalation pressure (Pep).

Control of the exhalation valve 120 may be obtained by applying pressure to a moving wall of the valve 120 making it possible, or otherwise, for the gas exhaled by the patient to be discharged to the outside.

In a known way, the controlling means comprise a compressor, for example of the vane or diaphragm type, for controlling the value of the positive exhalation pressure.

As it operates, the compressor makes it possible periodically to supply a determined volume of gas. It is necessary to arrange a storage chamber which forms a gas reservoir and makes it possible to increase and to stabilize the pressure of the gas supplied. An outlet orifice of the chamber is connected to the exhalation valve 120 so as in particular to apply a control pressure to its moving wall.

Small variations in the control pressure cause fluctuations of the moving wall of the valve 120 and instability in the positive exhalation pressure. This instability may cause the patient problems.

A compressor such as this does not allow optimum operation of the apparatus 10 for assisting with ventilation. Each time it supplies a determined volume of gas, the storage chamber is unable to completely stabilize the pressure, and this causes a variation in the positive exhalation pressure.

In addition, it is necessary to reach a compromise between the output of the pump and the stability of the positive exhalation pressure. What happens is that a compressor supplying a significant gas flow rate causes variations in the positive exhalation pressure which are greater than those caused by a compressor supplying a lower gas flow rate. However, a high gas flow rate is needed to cause the valve 120 to operate quickly, providing the patient with optimum comfort.

In order to overcome these drawbacks, the invention proposes for the controlling means 122 to comprise a fan consisting of a rotary electric machine, and a bladed wheel, in a similar way to the gas source 12 described previously.

Thus, the rotary electric machine of the fan is controlled by the control circuit so that the outlet pressure of the compressed gas corresponds to the value of the positive exhalation pressure.

Such a fan has low inertia, which allows it quickly to supply a high gas flow rate at a determined pressure. Thus, operation of the means 120 is rapid.

In addition, the outlet pressure of the fan is fairly constant, which makes it possible to dispense with the storage chamber and ensure optimum stability of the positive exhalation pressure.

In addition, the control circuit of the apparatus 10 controls the outlet pressure of the fan on the basis of the pressure of the gas exhaled by the patient. Thus, the positive exhalation pressure is independent of the flow rate of the gas exhaled by the patient, and of any value of leakage flow rate of the gas source 12.

A pipe 124 connects the controlling means 122 to the exhalation valve 120 so that the compressed gas applies a force to a moving diaphragm of the exhalation valve 120 to cause it to open when the pressure of the gas exhaled by the patient exceeds the positive exhalation pressure.

Figure 5:
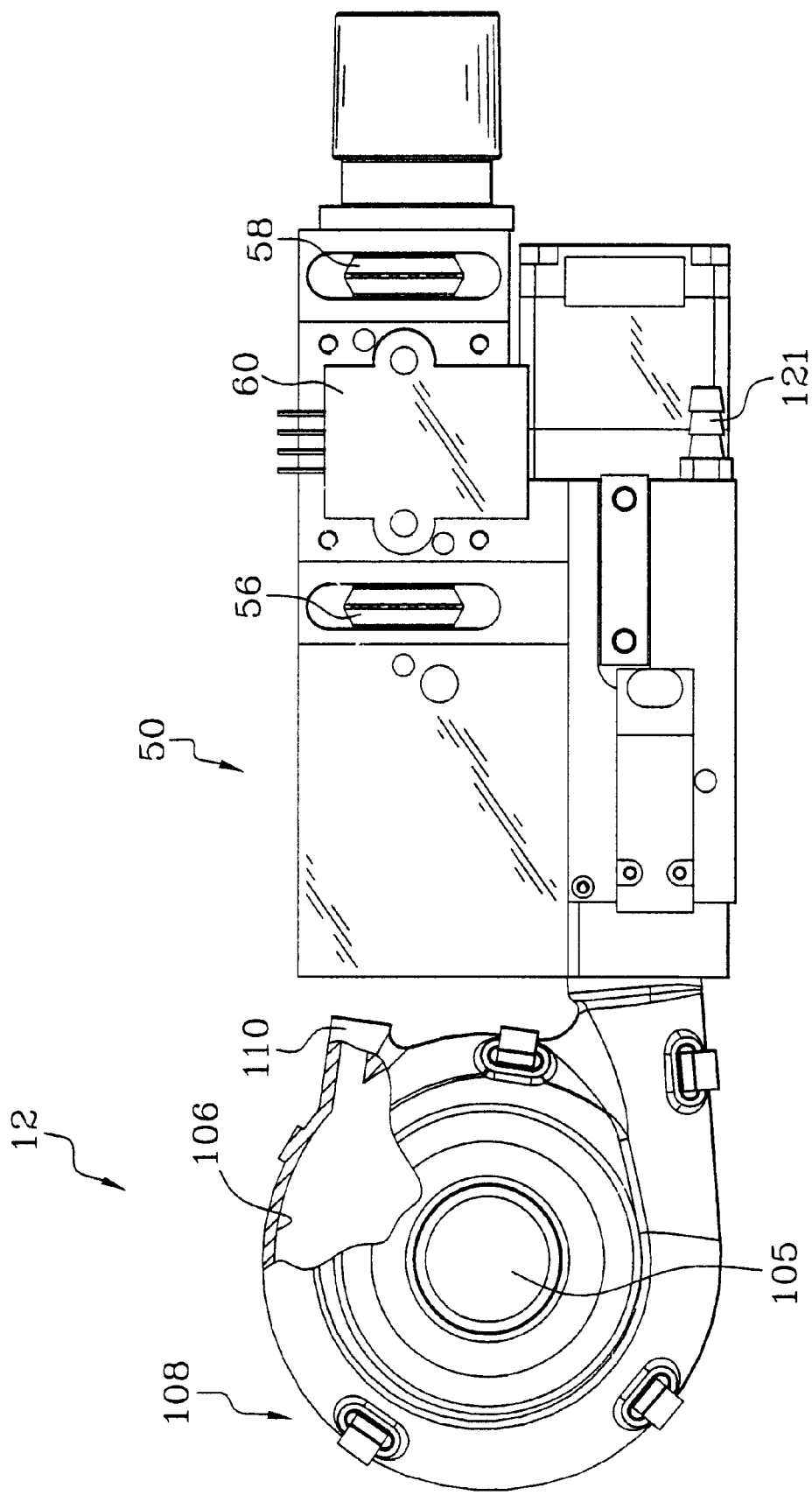
Figure 6:
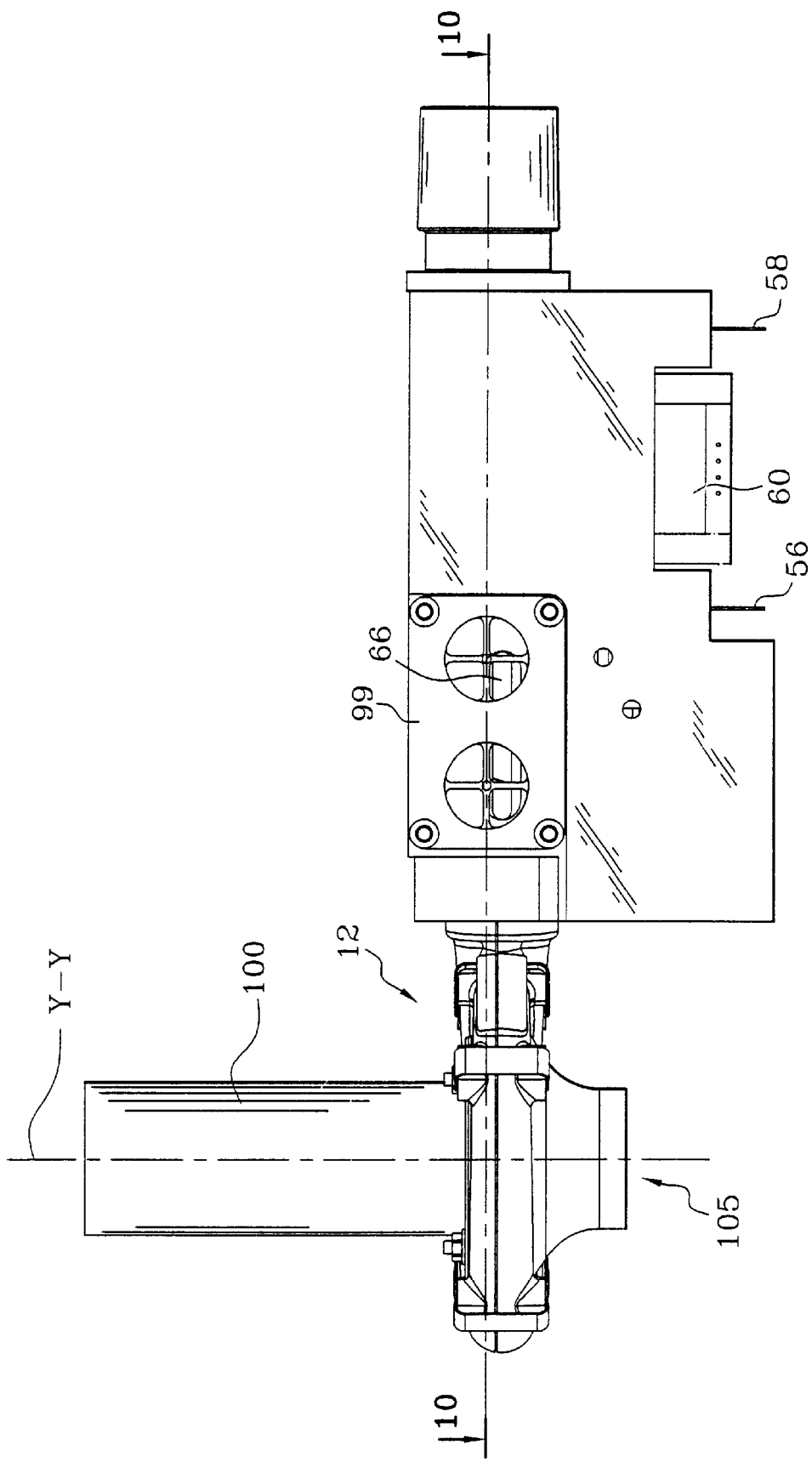
Figure 7:
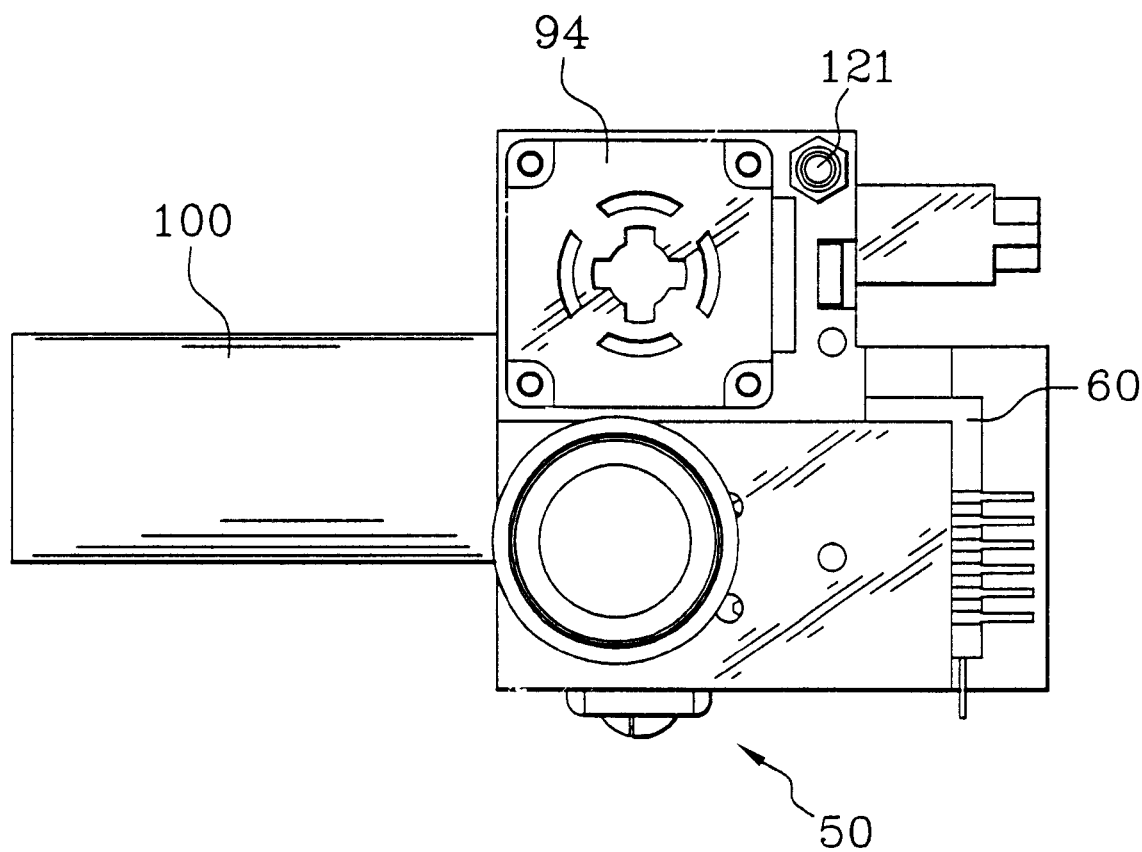
Figure 8:
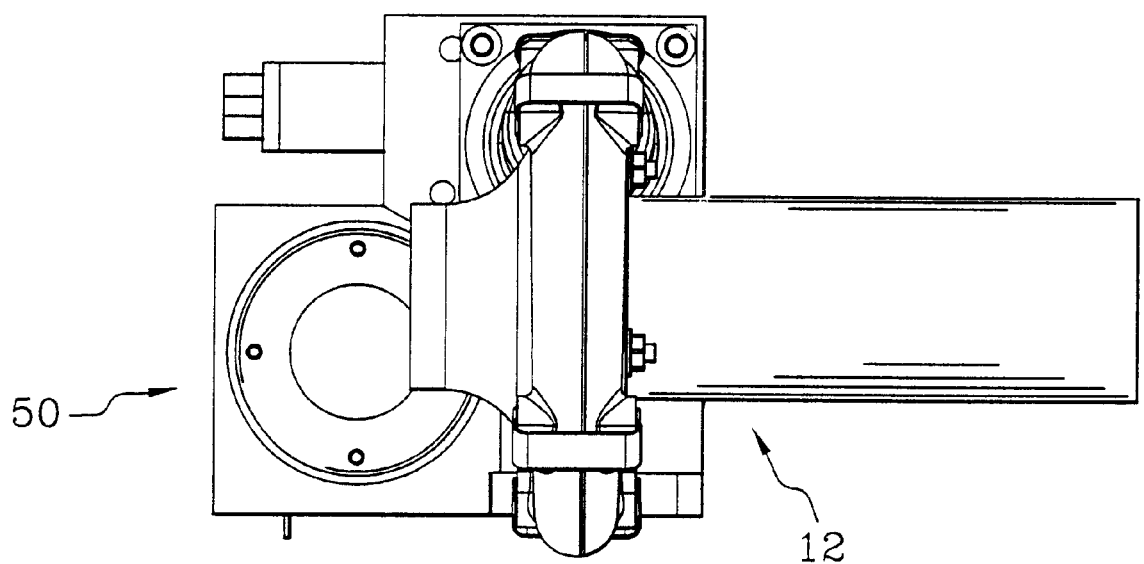

To make connections between the pipe 124 and the controlling means 122 easier, the distribution unit 50 comprises a connector 121, depicted in particular in FIGS. 5 and 7.

The pressure and the flow rate of the compressed gas flowing through the pipe 124 are very low. The pipe 124 can thus be flexible and of small size.

In order to monitor the air exhaled by the patient, the apparatus 10 for assisting with ventilation comprises measurement means 126 which determine the flow rate of the gas passing through the inhalation pipe during the exhalation phase. The determined values are then processed by the control means 34 so as to estimate the volume of gas exhaled by the patient.

The distribution unit 50 incorporates the measurement means 126 which here consist of two pressure sensors 125.

These two sensors 125 are connected to two pressure tappings 127 of the inhalation pipe 14 via two pipes 129.

The pressure tappings are arranged one on each side of a member 128 located near the mask 15 and the function of which is to cause a pressure drop. The control means 34 therefore determine the volume exhaled by the patient on the basis of the information representing the pressure difference, supplied by the two sensors 125.

Thus, when the apparatus 10 is equipped with a single circuit 118, the exhalation valve 120 and the two pressure tappings 127 are connected to the controlling means 122 and to the measurement means 126 by flexible small-sized pipes 124 and 129 respectively, so that the single inhalation circuit 118 is easy to handle, lightweight and not very bulky, allowing easy use of the mask 15.

In addition, the single circuit 118 uses components such as the exhalation valve 120 which are robust and inexpensive.

Figure 15:
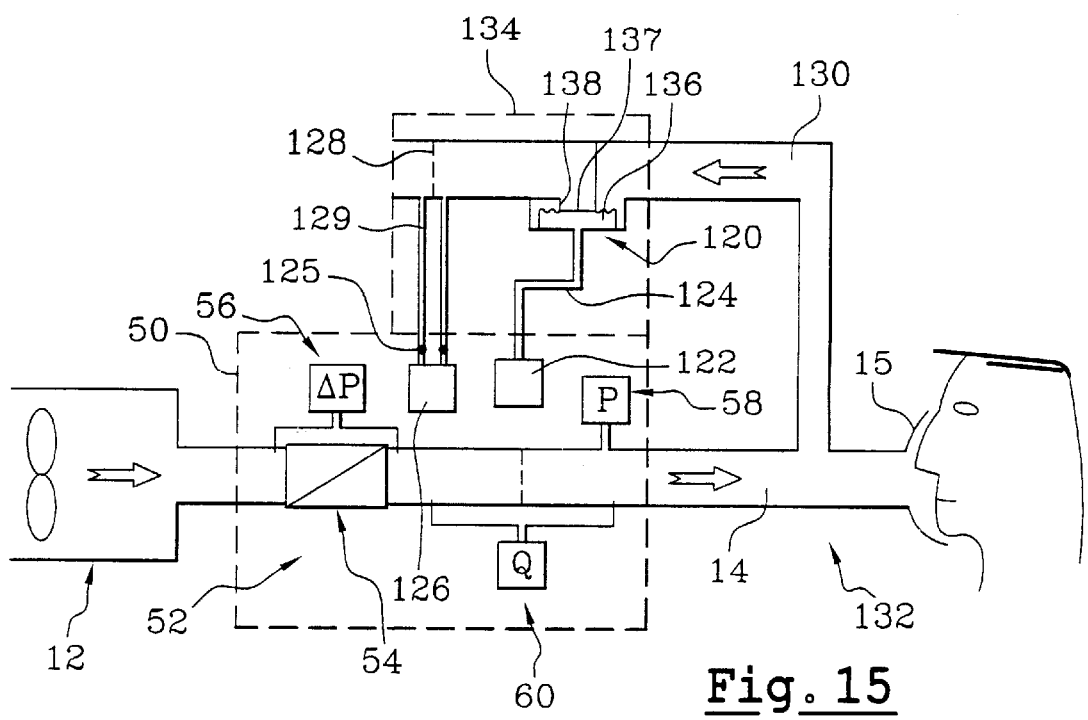
FIG. 15 is a view similar to the one depicted in FIG. 2, the apparatus for assisting with ventilation being equipped with a double circuit.

The distribution unit 50 comprising the controlling means 122, and the measurement means 126, may also be used for an apparatus 10 for assisting with ventilation comprising a circuit known as a "double circuit" 132 of the type depicted in FIG. 15.

The apparatus 10 for assisting with ventilation therefore comprises an inhalation pipe 14 and an exhalation pipe 130 which are joined together near the mask 15.

In this case, the downstream end of the exhalation pipe 130 comprises a module 134 which is fixed to the distribution unit 50.

The module 134 comprises the depression member 128 and an exhalation valve 120 which are connected to the measurement means 126 and to the controlling means 122 by, respectively, the pipes 124, 129 produced in a module 134.

Seals are fitted around the free ends of the pipes 124 and 129 so as to prevent any leakage that would disrupt the measuring of the exhaled volume or the control of the positive exhalation pressure of the exhalation valve 120.

As the pipes 124, 129 are very short, the value of the positive exhalation pressure and the measurement of the exhaled volume are very precise.

The apparatus 10 for assisting with ventilation, equipped with a double circuit 132, may be intended for patients whose state of health is critical. It is therefore necessary to eliminate any disruptions that may diminish its performance.

The two main causes of diminished performance are condensation in the exhalation pipe 130 and resistance of the exhalation valve 120 to opening.

What happens is that condensation in the exhalation pipe 130, particularly in the section located inside the module 134, may disrupt the measurement of the exhaled volume, and the operation of the exhalation valve 120.

In order to minimize or even eliminate condensation, particularly at the downstream end of the exhalation pipe 130, the module 134 is heated to cause water particles formed to evaporate.

In addition, the downstream end section of the exhalation pipe 130 is inclined overall so that its downstream free end is at the lowest point of the pipe 130, so as to encourage removal of condensate.

In general, the exhalation valve 120 of apparatus 10 for assisting with ventilation, equipped with a double circuit 132, is of the "balloon valve" form in which air pressure inside a balloon 136 forces a moving wall 137 thereof to press against an annular seat 138 to close off an inlet orifice of the valve. When the pressure of the inlet of the valve 120 is greater than the pressure inside the balloon 136, the valve 120 can then open, thus allowing gas to pass through the valve 120, generally towards the atmosphere.

A type of valve such as this allows good control over the positive exhalation pressure when in a steady state. However, during the phase in which the valve 120 is opening, the pressure there has to be in the exhalation pipe 130 has to be higher than the positive exhalation pressure. The difference between these two pressures results from the elastic deformation of the balloon 136.

Now, it is generally at the start of the exhalation phase that the flow rate exhaled by the patient is the greatest. The raised pressure brought about by the elastic deformation of the balloon may then cause the patient problems.

Thus, it is advantageous for the means 122 of controlling the positive exhalation pressure to be equipped with a system for assisting with opening the exhalation valve 120. Such a system makes it possible, during the phase of opening the exhalation valve 120, to apply a pressure which corresponds to the difference between the positive exhalation pressure and the pressure that is to be applied in order to cause the exhalation valve 120 to open.

The system for assisting with opening the exhalation valve 120 may also comprise an electromagnetic actuator, a moving part of which is connected to the moving wall 137. Thus, when the exhalation valve 120 opens, the moving part of the electromagnetic actuator applies to the moving wall 137 a force equivalent to the resistive force that is due to the elastic deformation of the balloon 136.

Such a system for assisting with opening the exhalation valve 120 makes it possible to combine the speed of the electromagnetic actuator, when opening the exhalation valve 120, and the stability with which the positive exhalation pressure is controlled by the means 122 when the exhalation valve 120 is open.

When the pressure to be applied in order to cause the exhalation valve 120 to open is higher than the positive exhalation pressure, the controlling means 122 have to apply a depression to the balloon 136.

The apparatus 10 for assisting with ventilation can thus be used with equal ease with a single circuit 118 or with a double circuit 132. The apparatus 10 can thus be used with equal ease in a hospital environment or in the home.

To make it easier to fit the single circuit 118 and the double circuit 132 on the distribution unit 50, the apparatus 10 for assisting with ventilation has connectors allowing the controlling means 122 and the measurement means 126 to be coupled with equal ease to the pipes 124, 129 respectively of a single circuit 118 or a double circuit 132.

The distribution unit 50 also comprises means, not depicted, for fastening the module 134.

The fastening means may be tappings into which threaded elements are screwed. They may also comprise elements which collaborate elastically with complementary elements of the module 134, so that the latter can be fastened to the distribution unit 50 by engagement of the complementary elements.

In an alternative, not depicted, the inhalation valve allows discharge to the atmosphere of at least some of the gas supplied by the gas source 12, during certain phases of the ventilation assist cycle of the apparatus 10, and particularly during the exhalation phase. Document FR-A-2 714 837 describes and depicts a valve of this type.

The invention proposes for the annular cylindrical wall of the tubular body of the inhalation valve to have a second opening or slot which is oriented more or less at right angles to the first opening. The second opening then allows the inside of the tubular body and the outside of the apparatus to be connected.

The profile of the front axial end edge of the skirt then has an overall V-shape.

According to this alternative form, the gas source provides a constant stream of gas, the stream transmitted to the patient then being regulated through the angular position of the skirt in the body.

The first and second openings are arranged one with respect to the other in such a way that the skirt can shut them off, or otherwise, fully or partially.

Specifically, for example, in the barometric ventilation respiratory assistance mode, during the inhalation phase, the skirt completely shuts off the second opening, so that all the stream of gas supplied by the source 12 is transmitted to the main inhalation pipe.

During the exhalation phase, the skirt completely (or partially in order to allow the passage of the leakage flow rate) shuts off the first opening.

To prevent a pressure increase at the outlet of the gas source, the angular position of the skirt allows the second opening to be opened to discharge the gas to the atmosphere.

Advantageously, the shape and position of the first and second openings, and of the skirt of the spool are such that the combined passage cross section for gas through the first and second openings is constant, irrespective of the phase of operation of the apparatus for assisting with ventilation.

What is claimed is:

1. Apparatus for assisting with ventilating a patient breathing in successive cycles, each having a phase of inhalation and a phase of exhalation, said apparatus comprising:
    a pressurized gas source, an outlet orifice of said pressurized gas source supplies a stream of pressurized gas intended to be transmitted to the upper airways of the patient;
    a pressurized gas stream distribution unit which comprises a transmission circuit which connects the outlet orifice of the gas source to a first free end of a main inhalation pipe, to the second free end of which is fixed a mask intended to be worn by the patient; and
    an inhalation valve for regulating the gas stream and which is interposed in the transmission circuit, and is controlled by a control circuit of the apparatus, and which is produced in the form of a rotary directional-control valve,
    wherein the inhalation valve for regulating the gas stream comprises a tubular valve body having a wall with a longitudinal oblong opening that allows the stream of gas from the outlet orifice of the gas source to be transmitted to the first free end of the main inhalation pipe and comprises a spool which is mounted so that the spool can turn in the body, said spool is closed at one axial end and has an axial end edge, at an opposite end to the closed end, said axial end edge has a profile that corresponds to a curve in the overall form of a spiral so that as the spool is turned, the passage cross section of the oblong opening allowing the transmission of the gas stream is varied progressively.

2. Apparatus (10) for assisting with ventilation according to claim 1, characterized in that the outlet orifice (107) of the gas source (12) opens into the first free end of a first hole (64), the second free end of which is plugged by the closed end of the spool (72) and in that the distribution unit (50) has a recess (68) which opens, on the one hand, opposite the longitudinal oblong opening (66) which it complements, and on the other hand, into a second blind hole (70) to the free end of which the first free end of the main inhalation pipe (14) is fixed.

3. Apparatus (10) for assisting with ventilation according to claim 1, characterized in that the spool (72) is turned by a motor (94), particularly of the stepping type, controlled by the control circuit of the apparatus (10).

4. Apparatus (10) for assisting with ventilation according to claim 1, characterized in that the spool (72) has a device (96) for indexing its angular position.

5. Apparatus (10) for assisting with ventilation according to claim 1, characterized in that the control circuit of the apparatus (10) controls the angular position of the spool (72) and the pressure supplied by the gas source (12) so that the passage cross section allows the predetermined volume of gas to be transmitted to the patient.

6. Apparatus (10) for assisting with ventilation according to claim 1, characterized in that the control circuit of the apparatus (10) controls the angular position of the spool (72) so that the passage cross section corresponds to the entirety of the oblong opening (66) and in that the control circuit of the apparatus (10) controls the pressure supplied by the gas source (12) so that the pressure of the gas in the inhalation pipe (14) is the predetermined gas pressure.

7. Apparatus (10) for assisting with ventilation according to claim 6, characterized in that the control circuit of the apparatus (10) controls the switching of the angular position of the spool (72) back and forth about a predetermined position that corresponds to the predetermined flow rate and controls the pressure supplied by the gas source (12).

8. Apparatus (10) for assisting with ventilation according to claim 1, characterized in that the pressurized gas source (12) comprises a rotary electric machine (100) controlled in terms of speed by the control circuit, a free end of the rotor (102) of which drives the rotation of a bladed wheel (104) which drives the gas stream through a guide volute (106) of a casing (108) when the rotary electric machine (100) is electrically powered.

9. Apparatus (10) for assisting with ventilation according to claim 8, characterized in that the casing (108) has at least one injection point (110), opening into the volute (106), for ejecting at least one compressed gas which is supplied by another upstream pressure source, at a second pressure higher than the first pressure, and in that the compressed gas at the second pressure is capable of driving the rotation of the bladed wheel (104) and of the rotor of the rotary electric machine (100) so that the pressurized gas is supplied to the patient at the first pressure and the rotary electric machine (100) acts as an electricity generator and produces electrical energy.

10. Apparatus (10) for assisting with ventilation according to claim 9, characterized in that the stream of at least one gas at a second pressure is injected into the casing (108) in a direction more or less tangential to the volute (106).

11. Apparatus (10) for assisting with ventilation according to claim 9, characterized in that the upstream pressure source at least partially consists of a pressurized gas circuit available in a hospital environment.

12. Apparatus (10) for assisting with ventilation according to claim 9, characterized in that the source of pressure comprises a pressurized gas reservoir.

13. Apparatus (10) for assisting with respiratory ventilation according to claim 12, characterized in that the reservoir is incorporated into the apparatus (10) for assisting with ventilation.

14. Apparatus (10) for assisting with respiratory ventilation according to claim 9, characterized in that the gas at the second pressure is made up at least partially of air.

15. Apparatus (10) for assisting with respiratory ventilation according to claim 9, characterized in that the compressed gas at the second pressure is made up at least partially of a therapeutic gas.

16. Apparatus (10) for assisting with ventilation according to claim 15, characterized in that the therapeutic gas is oxygen.

17. Apparatus (10) for assisting with ventilation according to claim 9, characterized in that means for regulating the pressure are inserted between the said other upstream pressure source and injection point (110).

18. Apparatus (10) for assisting with ventilation according to claim 9, characterized in that it comprises a valve for metering the compressed gas at the second pressure, the opening of which valve is controlled in proportion with the opening of the inhalation valve (54).

19. Apparatus (10) for assisting with respiratory ventilation according to claim 8, characterized in that the electrical energy supplied by the rotary electric machine (100), operating as a generator, at least partially powers the electricity-consuming systems of the apparatus (10).

20. Apparatus (10) for assisting with respiratory ventilation according to claim 9, characterized in that the electrical energy produced by the rotary electric machine (100), operating as a generator, powers and at least partially charges an accumulator battery of the apparatus (10).

21. Apparatus (10) for assisting with respiratory ventilation according to claim 9, characterized in that the electrical energy produced by the rotary electric machine (100) is more than the electrical energy consumed by the electricity-consuming systems, so that the apparatus (10) for assisting with respiratory ventilation is autonomous.

22. Apparatus (10) for assisting with respiratory ventilation according to claim 21, characterized in that the distribution unit (50) comprises controlling means (122) which can order the opening and closing of an exhalation valve (120) which is arranged with equal preference in the inhalation pipe (14) of a single circuit (116) or in the exhalation pipe (130) of a double circuit (132).

23. Apparatus (10) for assisting with ventilation according to claim 22, characterized in that, when it has a double circuit (132), the exhalation valve (120) is arranged in the module (134) which is fixed to the distribution unit (50) and comprises a pipe (124) for connecting the controlling means (122) to the exhalation valve (120).

24. Apparatus (10) for assisting with ventilation according to claim 22, characterized in that the controlling means (122) allow a positive exhalation pressure to be applied to the exhalation valve (120), and in that the positive exhalation pressure is provided by a fan.

25. Apparatus (10) for assisting with ventilation according to claim 24, characterized in that the distribution unit (50) comprises measuring means (126) which determine the flow rate of gas flowing, during the exhalation phase, through the inhalation pipe (14) of a single circuit (118) or through the exhalation pipe (130) of a double circuit (132).

26. Apparatus (10) for assisting with ventilation according to claim 25, characterized in that, when it has a double circuit (132) it comprises a module (134) which is fixed to the distribution unit (50) and comprises at least one pipe (129) connecting the measuring means (126) to the exhalation pipe (130).

* * * * *